United States Patent [19]
Wyrick

[11] Patent Number: 5,665,071
[45] Date of Patent: Sep. 9, 1997

[54] RELOADABLE AUTOMATIC OR MANUAL EMERGENCY INJECTION SYSTEM

[75] Inventor: Ronald E. Wyrick, Spokane, Wash.

[73] Assignee: Washington Biotech Corp., Spokane, Wash.

[21] Appl. No.: 670,630

[22] Filed: Jun. 26, 1996

Related U.S. Application Data

[63] Continuation of Ser. No. 243,641, May 16, 1994, Pat. No. 5,540,664, which is a continuation-in-part of Ser. No. 68,644, May 27, 1993, Pat. No. 5,358,489 issued Oct. 25, 1994.

[51] Int. Cl.$^6$ ............................................. A61M 5/20
[52] U.S. Cl. ........................... 604/134; 604/131; 604/135
[58] Field of Search ............................. 604/136, 135, 604/134, 208, 211

[56] References Cited

U.S. PATENT DOCUMENTS

| | | |
|---|---|---|
| 2,701,566 | 2/1955 | Krug . |
| 2,750,943 | 6/1956 | Dann . |
| 3,136,313 | 6/1964 | Enstrom et al. . |
| 3,712,301 | 1/1973 | Sarnoff . |
| 3,797,489 | 3/1974 | Sarnoff . |
| 3,880,163 | 4/1975 | Ritterskamp ............ 128/218 F |
| 4,085,489 | 4/1978 | Bordow . |
| 4,178,928 | 12/1979 | Tischlinger . |
| 4,214,584 | 7/1980 | Smirnov et al. . |
| 4,316,463 | 2/1982 | Schmitz et al. . |
| 4,723,937 | 2/1988 | Sarnoff et al. . |
| 4,755,169 | 7/1988 | Sarnoff et al. . |
| 4,874,385 | 10/1989 | Moran et al. . |
| 4,883,472 | 11/1989 | Michel . |
| 4,936,833 | 6/1990 | Sams . |
| 4,973,318 | 11/1990 | Holm et al. . |
| 5,009,645 | 4/1991 | Silver et al. . |
| 5,085,642 | 2/1992 | Sarnoff et al. . |
| 5,092,842 | 3/1992 | Bechtold et al. . |
| 5,114,406 | 5/1992 | Gabriel et al. . |
| 5,137,516 | 8/1992 | Rand ...................... 604/136 |
| 5,244,465 | 9/1993 | Michel . |
| 5,358,489 | 10/1994 | Wyrick . |
| 5,425,715 | 6/1995 | Dalling et al. . |

FOREIGN PATENT DOCUMENTS 0 577 448  1/1994  European Pat. Off. .

Primary Examiner—Sam Rimell
Assistant Examiner—Luke J. Yeh
Attorney, Agent, or Firm—Wells, St. John, Roberts, Gregory & Matkin, P.S.

[57] ABSTRACT

A reloadable automatic or manually usable medicine injection apparatus having a barrel which receives a syringe subassembly. The syringe subassembiy includes an ampule for housing fluid medication, a needle, a plunger stopper, and plunger shaft which allow removal and manual use. The injection apparatus includes a driver for forcing the syringe subassembly to inject the needle and displace fluid medication. The injection apparatus preferably includes a trigger handle, sheath remover, and removable stop system for delivery of multiple doses.

4 Claims, 7 Drawing Sheets

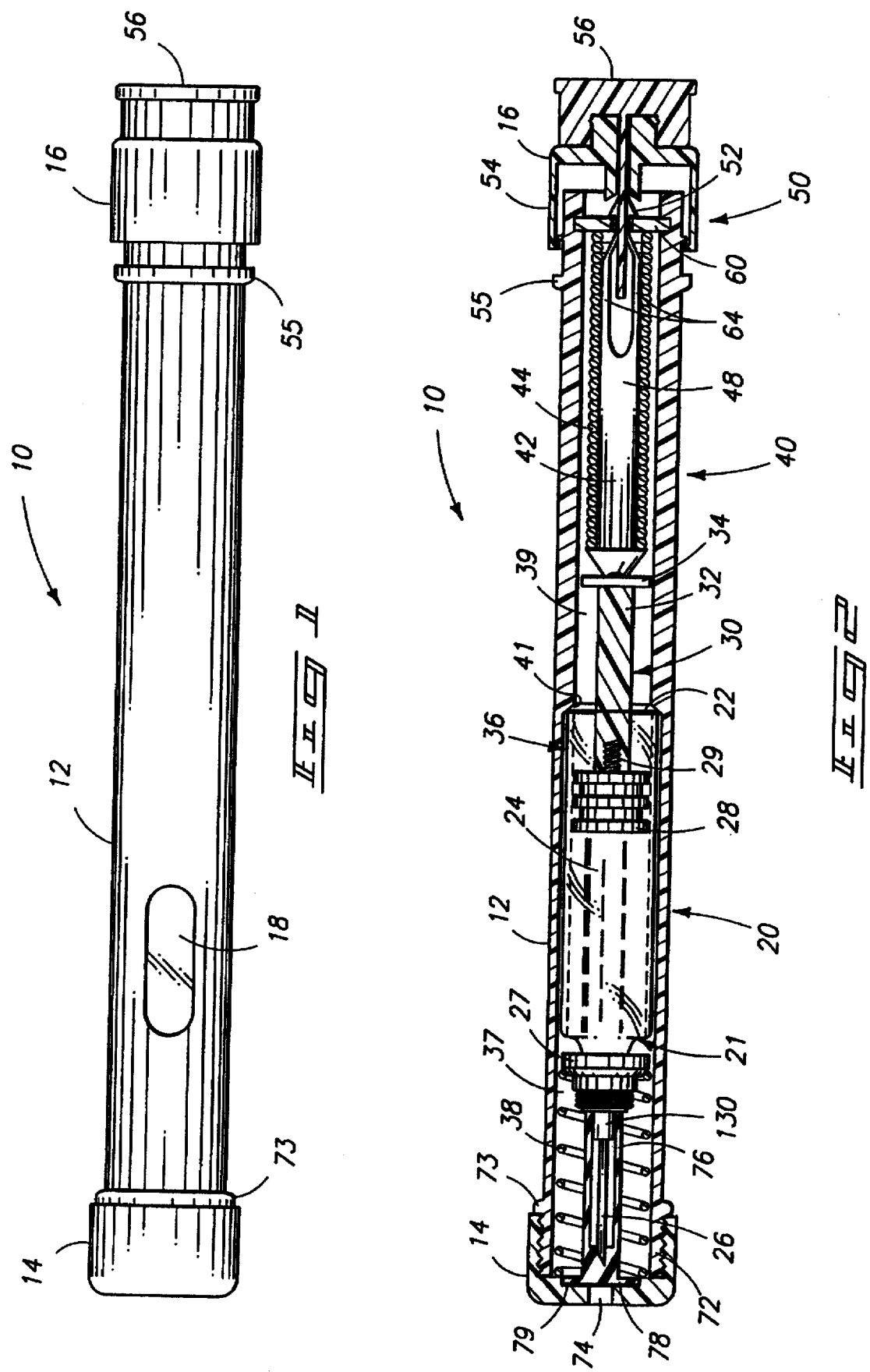

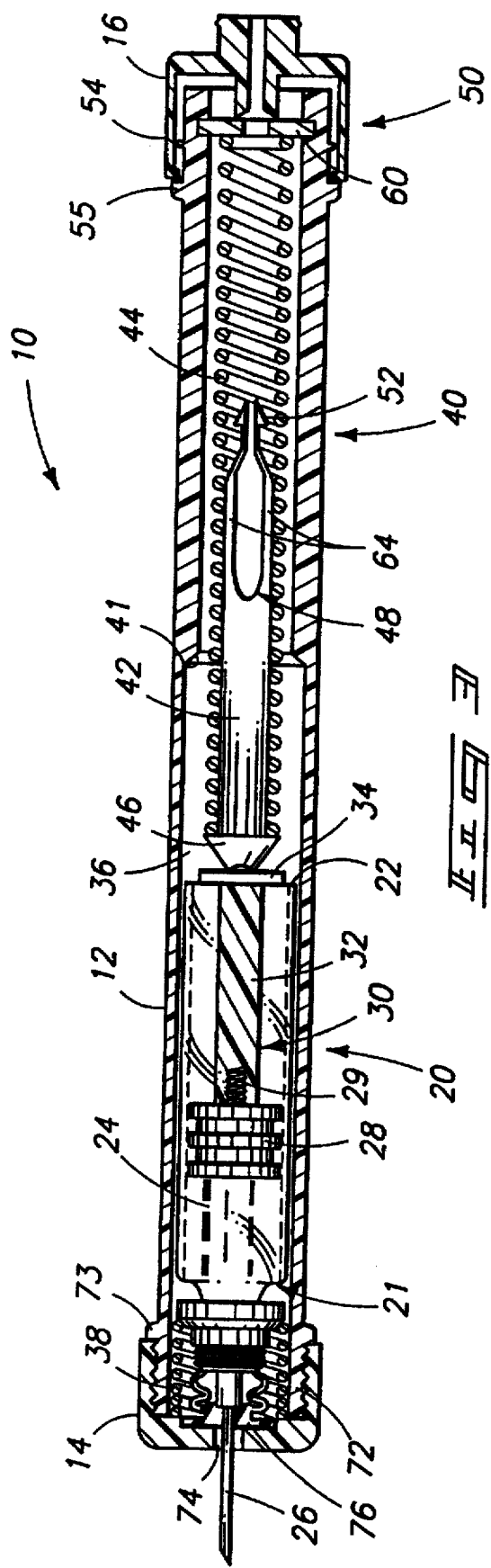
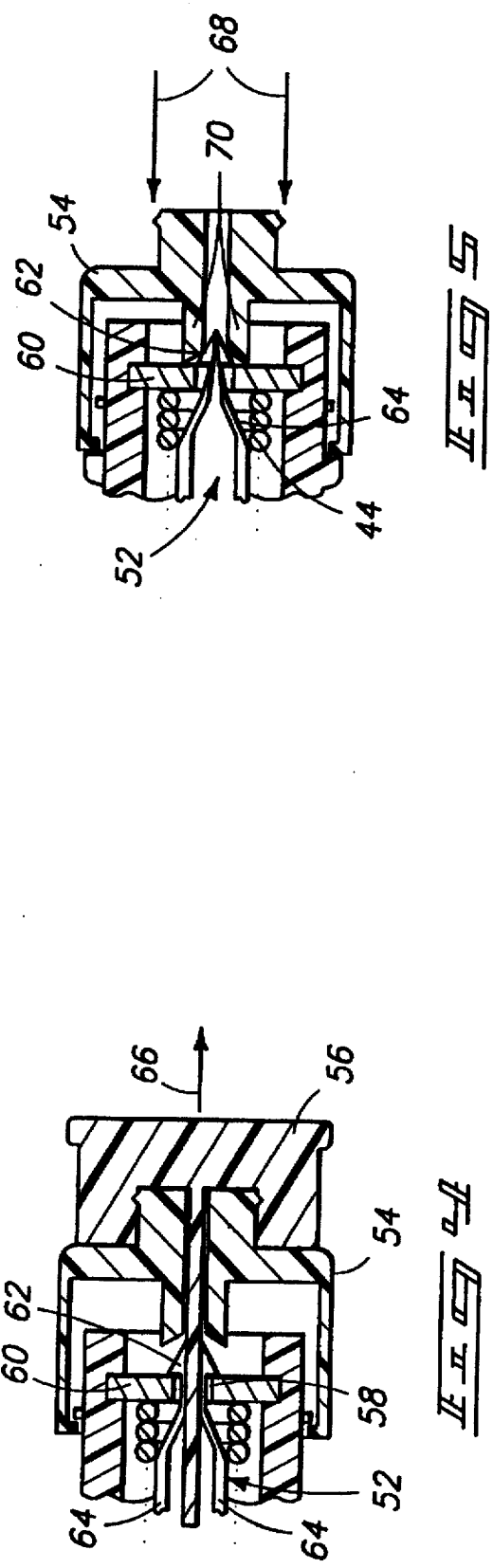

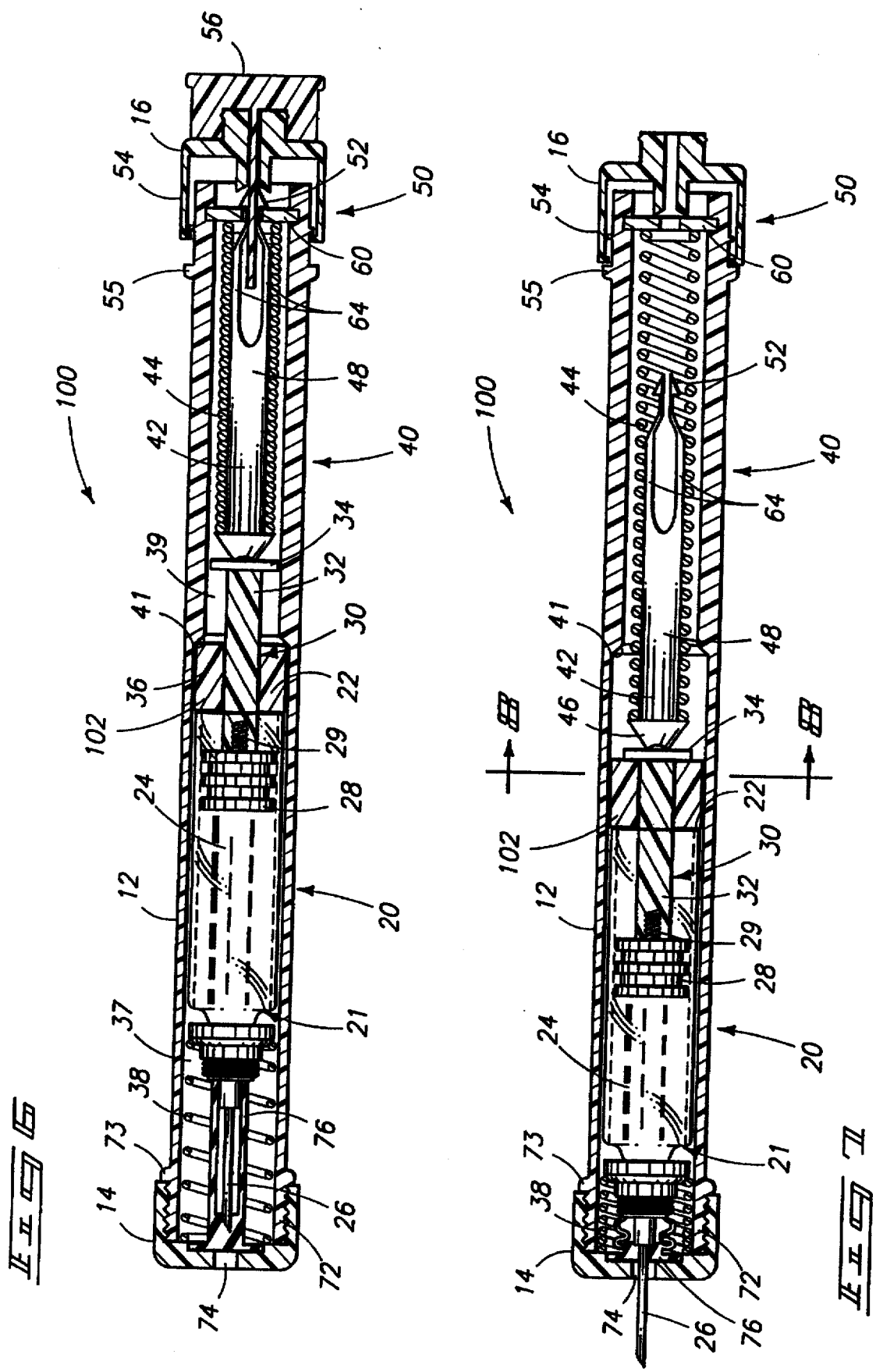

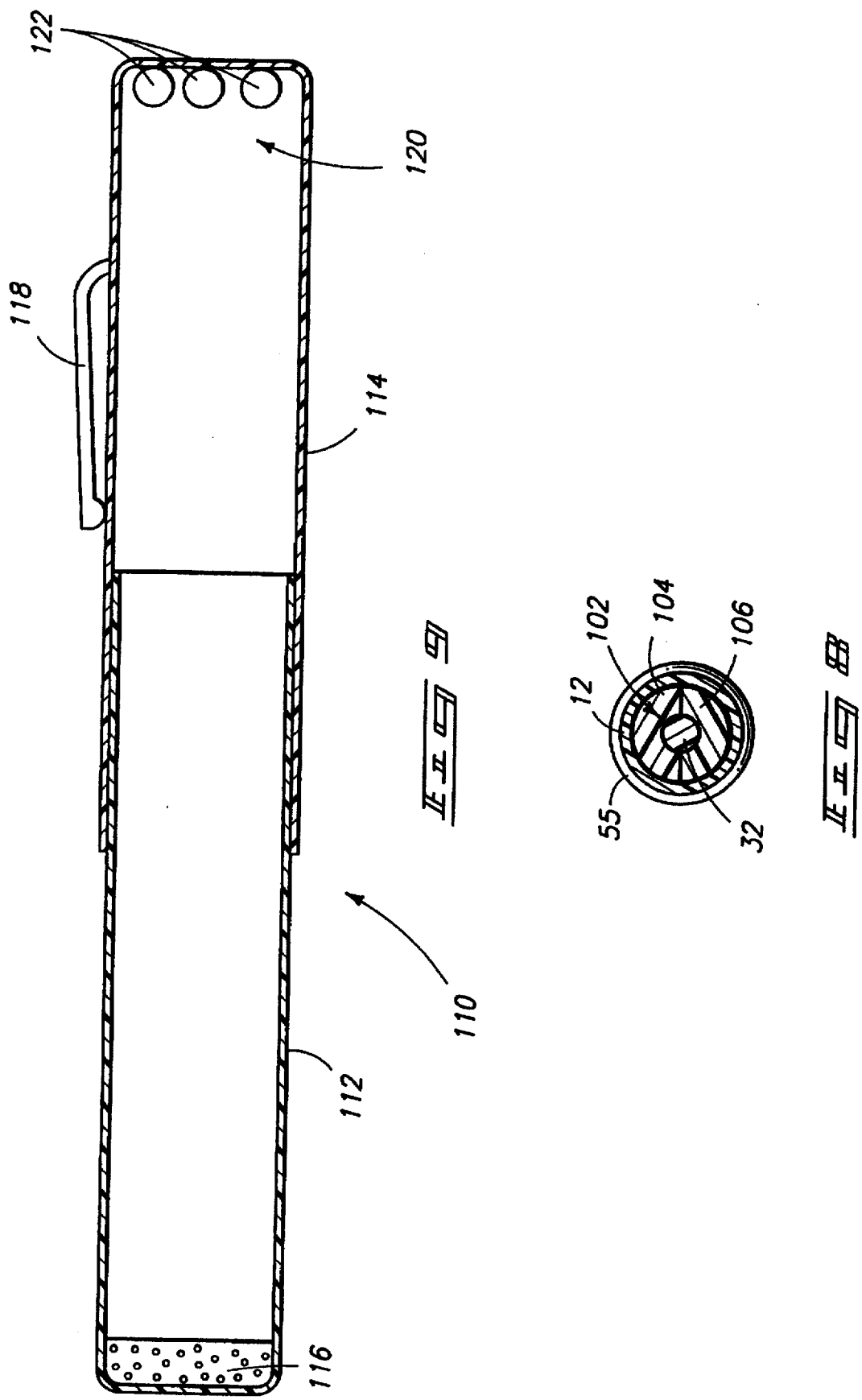

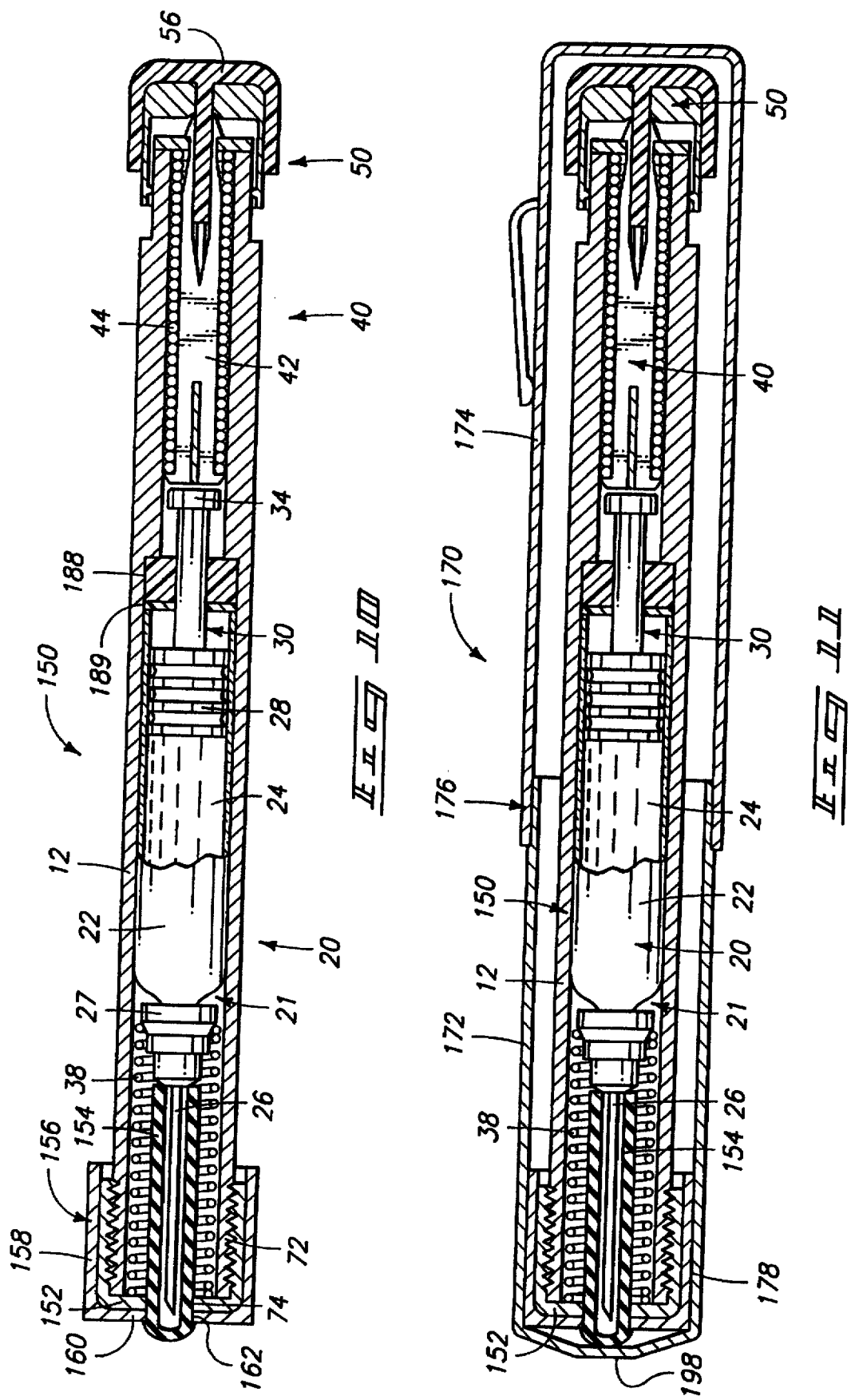

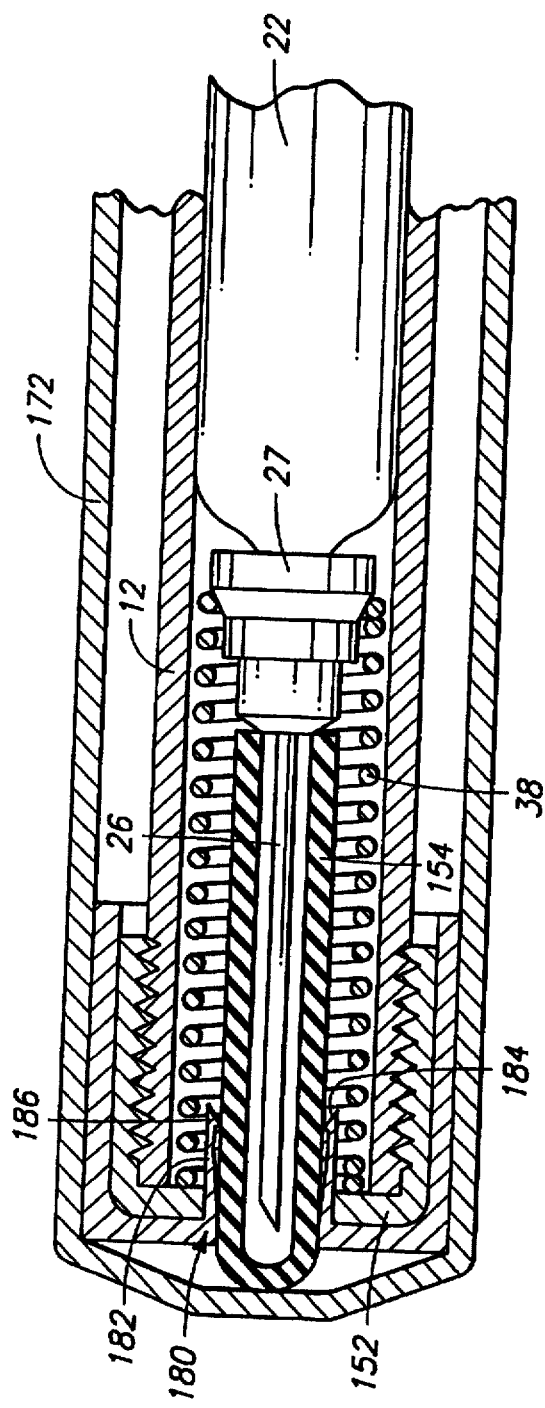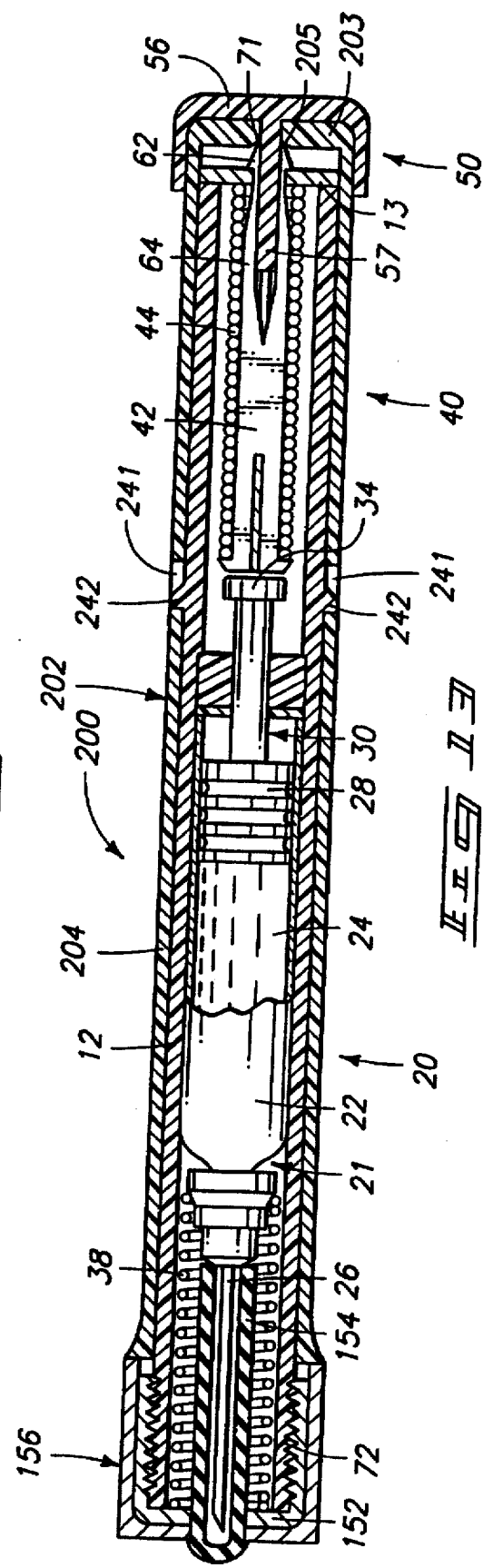

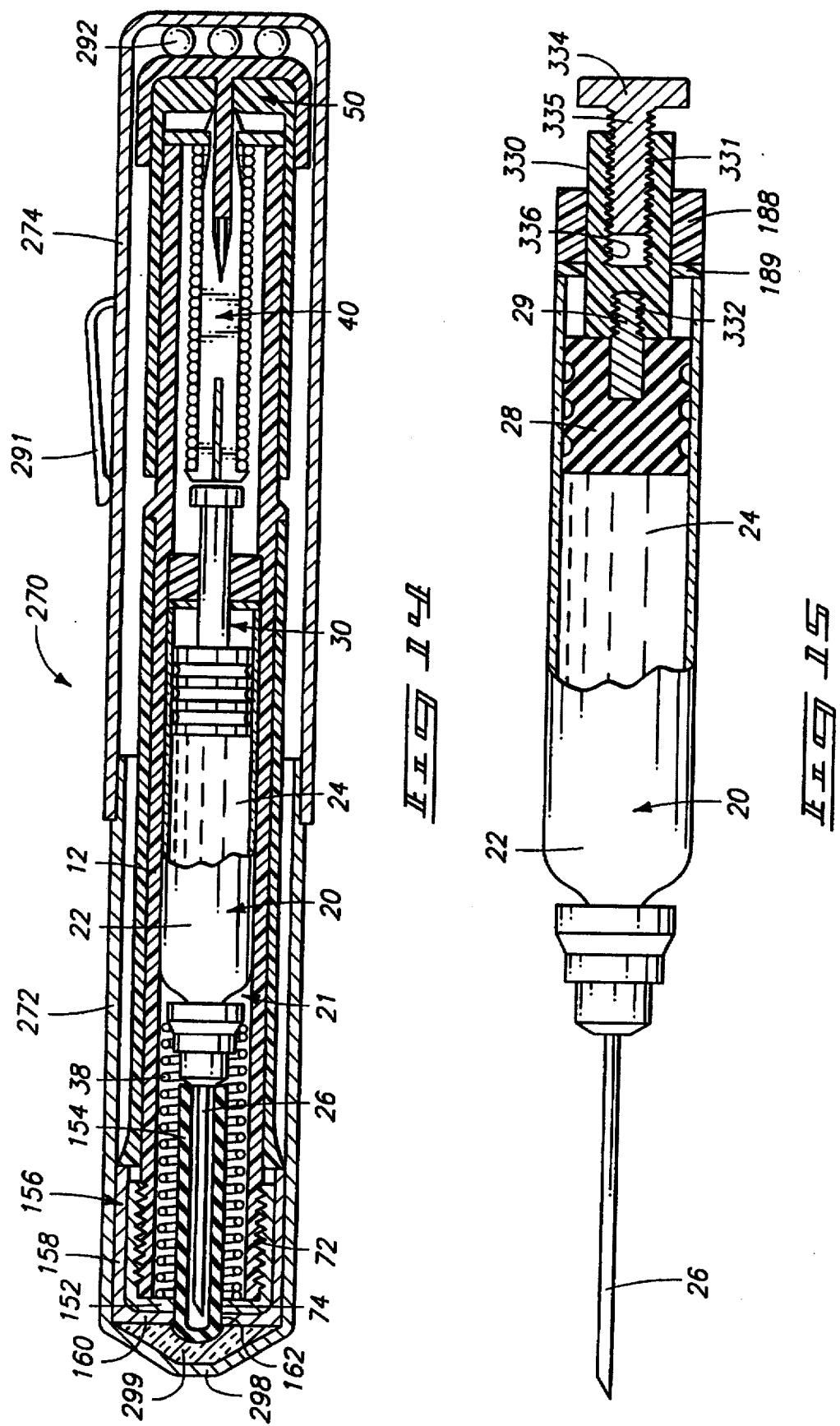

RELOADABLE AUTOMATIC OR MANUAL EMERGENCY INJECTION SYSTEM

CROSS-REFERENCE TO RELATED PATENT APPLICATIONS

This is a continuation of U.S. patent application Ser. No. 08/243,641 filed, May 16, 1994 now U.S. Pat. No. 5,540,664, which was a continuation-in-part application based upon U.S. patent application Ser. No. 08/068,644, filed May 27, 1993, now U.S. Pat. No. 5,358,489 issued Oct. 25, 1994.

TECHNICAL FIELD

This invention relates to automatic injection apparatuses for injecting fluid medications into bodily tissue.

BACKGROUND OF THE INVENTION

An automatic injection apparatus is a device which enables an individual to self-administer fluid medication by positioning and triggering the apparatus. The apparatus contains a measured dose of medication in a sealed sterile condition and is capable of storing the medication for an extensive period of non-use. The apparatus administers the self-contained dose automatically, so that the user does not need to visually insert the needle into tissue or depress a plunger, such as in a common syringe.

Automatic injectors are particularly advantageous in emergency conditions. Such injectors can carry: antidotes for nerve gas for use during emergency chemical warfare conditions; insulin for diabetes; epinephrine for allergic reactions; or analgesics.

An automatic injector apparatus commonly includes an elongated tubular casing and a medicine "container". The medicine container contains a dose of fluid medication. Also included is a needle for injecting the medication into the user. The injector further has a trigger mechanism which causes the needle to penetrate the user's tissue and inject the medication from the container.

Typical automatic injection apparatuses have a drawback in that they administer a single, one-time dose of medication and are not reusable. After this single use, the entire apparatus is discarded. This results in high cost and waste.

Another drawback is the relatively short storage life of some medications. The storage life of a medication is generally less than the useful life of the automatic injection apparatus. Automatic injectors are expected to be stored for long periods of time, often 5 years or more. Unfortunately, many medications do not have a comparable storage life. For example, some medications have storage lives of 1–2 years or less. The medicine could thus become ineffective before the injector is used, resulting in the wasteful disposal of unused injection apparatuses. This also contributes to high costs.

The inability of automatic injection apparatus to be reloaded causes substantial additional costs in other ways. Storage of integrated one use automatic injections is made more complicated and stock must be carefully inventoried and tracked for dates of use. Medicines needing or best stored under particular conditions (refrigeration) are typically unavailable due to the bulk of the injection apparatus. Medicines used in automatic emergency injectors are also inventoried in addition to inventories of medications used in hospitals. These factors become particularly troublesome and costly for the military because of the logistical problems, storage considerations, and tremendous quantities involved.

Another very serious limitation is that prior automatic injectors are not capable of manual injection in instances where they fail. Such failures can occur for a number of reasons. The syringe needle may not properly deploy so it is impossible to cause injection. Another potential failure involves a malfunction which does not eject the medicine from the needle. Malfunction can also occur with respect to the trigger and driving mechanisms. Whichever type of failure occurs it can be life-threatening in a substantial number of cases.

Prior injectors are manufactured as a single, integrated system that provides one application of medicine, and is then discarded. However, if the trigger, firing, syringe or other mechanism fails and the injection is not administered, the user cannot access the medication contained within the sealed unitary casing. Even if the user can get at the medicine vial, the internal components are not capable of being used manually to effect an injection of the medicine. This inability to use internal components of some prior art designs results from the fact that there is either no plunger in the ampule or syringe assembly, or the plunger is a part of the driving mechanism and the syringe cannot be removed and accessed when the injector is taken apart. Thus the prior injectors pose a risk that due to mechanical failure medication will not be administered.

This invention provides an automatic injection apparatus in which the injection apparatus can be loaded just prior to use, or alternatively sold already loaded. The injection apparatus can be loaded with a variety of medications as needed for the particular situation, and can latter be reloaded to refreshen the medication or change medications. The apparatus can be reloaded numerous times with cartridges commonly used in hospital inventories so that duplicate inventories are not required and better storage conditions are possible. As individual cartridges are used or the medicine contained therein becomes ineffective, the user simply replaces the cartridge with a new one without disposing of the injector. In this manner, only the inexpensive cartridges are replaced, and not the entire apparatus. This can reduce the costs significantly. Furthermore, the injector allows access and removal of a syringe subassembly by the user. The syringe subassembly can be used to provide a manual injection in the event that the injector or cartridge fails, or in the event that the user simply desires to apply the injection manually. The described system also includes embodiments which have dual dose capability for second dose administration. The second dose can be either automatically injected or manually injected.

BRIEF DESCRIPTION OF THE DRAWINGS

Preferred embodiments of the invention are described below with reference to the accompanying drawings. The same reference numerals are used throughout the drawings to reference like components and features. The drawings are briefly described below.

FIG. 1 is a side view of a reloadable, automatic injection apparatus according to this invention.

FIG. 2 is a longitudinal sectional view of the FIG. 1 apparatus and shows a syringe subassembly loaded in a barrel of the apparatus. FIG. 2 illustrates the apparatus in a cocked position with the syringe subassembly completely within the barrel.

FIG. 3 is a sectional view of the apparatus similar to that of FIG. 2 and illustrates the apparatus in an extended position with the syringe subassembly partially protruding from the barrel.

FIG. 4 is an enlarged partial sectional view of an end of the FIG. 2 apparatus and illustrates a safety mechanism of this invention.

FIG. 5 is an enlarged partial sectional view similar to FIG. 4 with a safety piece removed and the trigger mechanism depressed.

FIG. 6 is a longitudinal sectional view of an apparatus according to another preferred embodiment of this invention. FIG. 6 illustrates the apparatus in a cocked position with the syringe subassembly completely within the barrel.

FIG. 7 is a longitudinal sectional view of the apparatus similar to that of FIG. 6 and illustrates the apparatus in an extended position with the syringe subassembly partially protruding from the barrel.

FIG. 8 is a cross-sectional view of a stop collar employed in the FIG. 6 apparatus.

FIG. 9 is a longitudinal sectional view of a carrying case for storing and carrying a reloadable injection apparatus according to this invention.

FIG. 10 is a longitudinal sectional view of an apparatus according to yet another preferred embodiment of this invention having a sheath remover mounted to the barrel.

FIG. 11 is a longitudinal sectional view of the FIG. 10 apparatus stored within a carrying case of this invention.

FIG. 12 is an enlarged, partial longitudinal sectional view of an injector system similar to the apparatus of FIG. 11 in modified form. The injector is shown within a carrying case and shows a modified sheath remover in more detail.

FIG. 13 is a longitudinal sectional view of an apparatus according to still another preferred embodiment of this invention having a trigger handle.

FIG. 14 is a longitudinal sectional view of the apparatus of FIG. 13 stored within a carrying case of this invention.

FIG. 15 is an enlarged view of an alternative cartridge made in accordance with this invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

FIG. 1 shows a reloadable, automatic injection apparatus 10 according to this invention. The injection apparatus or "injector" has an elongated body or barrel 12 which extends between a first, distal or end cap 14 and a second, proximate or trigger end cap 16. Barrel 12 is a substantially cylindrical, hollow tube and is preferably formed of a hard, durable material, such as metal or plastic. End caps 14 and 16 are likewise formed of a hard, durable material. Barrel 12 has an elongated, longitudinally aligned window 18 formed therein to permit visible access to the interior of the tube. Window 18 may be open, with no material, or preferably consists of a clear material, such as transparent plastic.

FIGS. 2 and 3 show apparatus 10 in more detail. Apparatus 10 is designed to house a replaceable, disposable syringe subassembly 20. A principal component of subassembly 20 is a medicament cartridge 21. Cartridge 21 includes an ampule or medicament container 22 for housing and containing a fluid medication 24. Ample 22 is preferably a small glass or plastic vial that contains a measured amount of medication. The amount of medication (such as antidotal medicant, antibiotics, epinephrine, insulin, etc.), varies depending upon the medication and anticipated usage conditions. Cartridge 21 also has a hypodermic needle 26 mounted to the distal end of ampule 22 using a needle mounting cap 27. Cartridge 21 further has a fluid tight plunger which includes a stopper 28 which fittingly engages and slides within ampule 22. Stopper 28 is preferably formed of a rubber or elastomer material and has a plunger connector in the form of a mounted peg or threaded extension 29. The plunger connector faces outwardly and as shown extends outwardly from stopper 28. The structure of cartridge 21 is well-known and commercially available. Examples of preferred cartridges of this construction are manufactured under the trademark TUBEX by Wyeth Laboratories, Inc. and under the trademark DOSETTE by Elkins-Sinn.

The plunger of the syringe subassembly also includes a detachable plunger shaft 30. Plunger shaft 30 is detachably connected to stopper 28 using a suitable plunger shaft detachable coupling. While a threaded coupling is preferred, other common techniques for providing a detachable connection between plunger 30 and stopper 28 can be employed. As shown, the coupling includes a threaded extension 29 received within a threaded receptacle formed in the inner end of the plunger shaft. Plunger shaft 30 includes a stem 32 and a shaft head formed as a shoulder or flange 34. Plunger shaft 30 is preferably formed of a rigid material, such as plastic or metal.

Syringe subassembly 20 also preferably includes a protective sheath 76 disposed within barrel 12 around needle 26 of cartridge 21. The tip of needle 26 is slightly embedded in the head of the sheath to protect the sharp point and to seal the needle opening from contaminants. The head of the sheath has a flange 78 received in a receptacle 79 of cap 14. The sheath has a tubular portion which extends from the head and is received upon a needle sleeve portion 130 of the needle cap 27. Sheath 76 thereby provides a protective isolating cap that maintains the sterility of the needle until use occurs. Syringe subassembly 20 is inexpensive to manufacture and is designed to be disposed of once the medication 24 has been injected into the user.

According to this invention, reloadable injection apparatus 10 is designed to automatically deploy and discharge cartridge 21. However, in the event that the apparatus fails, the user can still administer the injection manually using the demountable syringe subassembly 20. Syringe subassembly 20 can be easily unloaded from injection apparatus 10 and can operate as a self-contained manually operated syringe in the event that the injector is damaged and will not fire. This aspect of the invention is advantageous over prior art injectors which are completely encased and do not permit access to or removal of the inner medicant capsule.

Barrel 12 of reloadable injection apparatus 10 is tubular and defines an internal cavity 36 with a first or cartridge chamber 37, sized to receive syringe subassembly 20, and an adjacent second or driver chamber 39. In the preferred form, chamber 37 has a circular cross-section with a diameter that is slightly larger than the diameter of ampule 22 so that the syringe subassembly can easily slide within cavity 36 from a first or storage position shown in FIG. 2 into a second or deployed position shown in FIG. 3. Cartridge chamber 37 is slightly larger in cross-section than second chamber 39. Preferably, chamber 37 tapers into chamber 39, thereby defining a tapered shoulder 41.

Automatic injection apparatus 10 also includes a driver 40 for injecting the needle 26 and discharging medication from the cartridge. Driver 40 is constrained in a cocked position and controllably released by a driver release mechanism 50.

Apparatus 10 also includes a secondary or biasing spring 38 which biases the syringe subassembly 20 away from the muzzle end. The syringe subassembly is preferably biased against shoulder 41 so that needle 26 is better protected against inadvertent deployment. Shoulder 41 also prevents the subassembly from shifting toward the driver, relative to the plunger, and causing premature discharge of the fluid within the barrel during a situation, for example, when the apparatus is accidentally dropped. Biasing spring 38 also acts as a suspension and shock absorber with sheath 76 for safely maintaining the subassembly within the tubular casing during transportation and conditions which may cause the subassembly to move or bounce.

Driver 40 includes a longitudinal bar 42 that is slidable within cavity 36 of barrel 12 between a cocked position (FIG. 2) and one or more extended positions (FIG. 3). Driver 40 also has a primary or drive spring 44 for biasing and forcing bar 42 toward an extended position. Driver bar 42 is preferably a rigid piece made of plastic or metal that extends axially within barrel 12. Bar 42 has a ramming or contact head 46 that abuts against plunger shoulder 34 in the cocked position and a tail portion 48. Head 46 also forms a drive spring engagement shoulder against which the drive spring bears. Drive spring 44 is axially aligned with the syringe subassembly and is coiled about bar 42. Driver 40 is positioned within driver chamber 39 of barrel cavity 38 when the driver is in a cocked position.

Driver release 50 holds driver 40 in the cocked position until the user is ready to administer the injection. Driver release 50 includes a catch 52, a trigger 54 for releasing the catch when the trigger is activated or depressed. The driver release also includes a safety 56 for preventing activation of the trigger and release of the catch. Trigger 54 is embodied as end cap 16 and is displaceable relative to barrel 12 from a rest or extended position into a depressed position where it abuts an annular flange 55 on the exterior of barrel 12. Trigger 54 fires the apparatus during its travel between the rest and depressed positions.

FIGS. 4 and 5 illustrate the driver release 50 in more detail. Catch 52 consists of a detent mechanism for releasibly coupling the driver to the driver release. The detent mechanism of catch 52 consists arrow-shaped or barbed tips 62 on multiple prongs 64 (provided on the tail portion 48 of bar 42). The prongs extend through a catch aperture 58 and latch to an end wall 60 of barrel 12. End wall 60 is preferably a metal annular disk molded into the plastic barrel 12, but can be a plastic end piece integrally molded with barrel 12. Prongs 64 are constructed to deflect from a normal, radially expanded position shown in FIG. 4 to a radially constricted position shown in FIG. 5 to enable the tips 62 to pass through aperture 58. The prongs are controllably deflected into the constricted position by the trigger piece 54 as explained below.

A safety pin 56 is inserted centrally of the multiple prongs 64 and through aperture 58 to retain the prongs in the expanded position so that the tips remain caught behind end wall 60. Safety pin 56 is removable from the apparatus 10 in the direction illustrated by arrow 66 (FIG. 4). Safety pin 56 is in suitable connection with trigger 54 to prevent the safety from prematurely popping off the end but allowing manual detachment.

Trigger 54 is depressed or activated by an external force (such as depression by the user's thumb) in the direction illustrated by arrows 68 in FIG. 5. Trigger 54 has pushing member 70 which moves toward and engages external sloped surfaces on tips 62 as the trigger is depressed. The pushing member preferably has a beveled internal surface which is complementary to the sloped surfaces of tips 62. The pushing members 70 force the tips together until they clear end wall 60 and escape through aperture 58. At this point, driver 40 is released and drive spring 44 powers the driver through barrel 12 to sequentially deploy and inject the needle and then discharge the medication through the injected needle.

Returning to FIGS. 2 and 3, left end cap 14 is detachably connected to barrel 12 to permit loading and unloading of syringe subassembly 20. In the preferred form, removable cap 14 and muzzle end 72 of barrel 12 are provided with complementary threads so that removable cap 14 can be screwed onto barrel 12, although other coupling arrangements can be employed. Cap 14 can be twisted onto barrel 12 until it reaches annular flange 73 formed on the exterior of barrel 12. Cap 14 substantially closes cavity 36 when connected to barrel 12 and alternately, opens the cavity when detached from the barrel to allow removal of the syringe subassembly. Removable cap 14 has an aperture or needle passageway 74 formed therein through which needle 26 of cartridge 21 can extend when the user operates the injection apparatus 10 and the syringe subassembly is deployed (FIG. 3).

Sheath 75 covers aperture 74 to prevent contamination of the needle 26. Sheath 76 is preferably formed of a deformable material, such as rubber, which can buckle under the force of drive spring 44 of driver 40 as illustrated in FIG. 3. A flange portion of sheath 76 abuts the inner surface of cap 14 and the head of the sheath is pierced by needle 26 when the syringe subassembly is moved through the barrel by the driver. Cap 14 has a stepped interior surface for accommodating the biasing spring 38 and the flange portion of sheath 76.

The general operation of this invention will now be described with reference to FIGS. 2 and 3. After construction, an empty injection apparatus 10 is suitable for storage for an extended length of time. Individual syringe subassemblies containing different types of medication are manufactured and stored separately according to their prescribed shelf lives. If the medication in the syringe subassemblies exceeds the potency expiration date, the individual subassembly can be discarded. One technique for manufacturing the subassemblies is to simply modify existing cartridges, such as TUBEX and DOSETTE cartridges, with a sheath and detachable plunger such as described herein. In this state, a user can manually administer an injection using the subassembly. This is done by removing the sheath, injecting the needle, and manually depressing the plunger in the typical fashion.

For automatic injection, a desired subassembly of a selected medicine is loaded into the automatic injection apparatus before the time of foreseeable potential use. Cap 14 is first removed from muzzle end 72 of barrel 12. If not already cocked, then a suitable rod can be extended up the cavity to force the driver into the cocked position of FIG. 2. The safety 56 can then be inserted. Then the syringe subassembly 20 is loaded into barrel 12 through the muzzle end and oriented therein so that the sheathed needle points outward toward the muzzle end. Biasing spring 38 is slid over sheath 76 and the cap 14 is screwed back onto the barrel. In this condition, apparatus 10 is in its cocked state with the subassembly safely retracted within the barrel casing as illustrated in FIG. 2. Apparatus 10 is now loaded and ready for use.

Window 18 in barrel 12 enables the user to view the cartridge and medication. From this visual inspection, a user can quickly determine the relative positioning of the plunger, the dosage level, and whether the medicine has become defective (for example, as ascertainable by clouding or a color change).

To fire apparatus 10, safety 56 is removed and trigger 54 is depressed to release catch 52. The energy stored in drive spring 44 of driver 40 is released, forcing subassembly 20 through barrel 12. Needle 26 pierces the head of sheath 76 and is driven out through passageway 74 in cap 14. Simultaneously, the tubular portion of sheath 76 buckles and secondary spring 38 contracts under the force of drive spring 44. Syringe subassembly 20 halts when it reaches the end of the barrel after it has traveled an effective distance to properly insert the exposed needle into the tissue of the user. The fully contracted secondary spring 38 acts as a stop deployment against the ampule 22 or needle cap 27.

After the syringe assembly is deployed into an injection position, the thrusting force of driver 40 continues and depresses plunger 30. This causes cartridge plunger 28 to move and displace fluid medication out through hypodermic needle 26. The plunger depresses until shoulder 34 abuts an end of ampule 22 or is otherwise stopped. The apparatus and cartridges are designed such that the distance of plunger travel is precise for an injection of a prescribed dosage of medication.

After the injection is complete, the user can withdraw the apparatus and needle. The fired apparatus can then be reloaded. To accomplish this, cap 14 is simply detached and the exhausted syringe subassembly is removed and discarded. Driver 40 is recocked by inserting a thin instrument (such as a screw driver, pen, or pencil) down the barrel and pushing bar 42 against the force of spring 44 until the barbed tips constrict and pass through aperture 58 and then spread to lock behind wall 62 (FIG. 4). Safety 56 can be reinserted at this point to prevent undesired firing. A new syringe subassembly containing the same or different medicine can then be inserted into the barrel and the cap reattached.

FIGS. 6–8 show a reloadable injection apparatus 100 according to another preferred embodiment of this invention. Apparatus 100 is designed to administer multiple (typically, two) injections using the same syringe subassembly. Apparatus 100 is very similar to apparatus 10 of FIGS. 2–5, and the same reference numerals are used to identify like components. Only the different features of this apparatus will be described in detail.

Apparatus 100 includes a removable stop 102 for halting movement of driver 40 at an extended position after it has been released. Stop 102 is provided within barrel 12 and positioned at least partially around plunger stem 32 of syringe subassembly 20. Stop 102 is radially sized to abut against the end of ampule 22. Stop 102 has a predetermined length to provide approximately equal dosages for each injection with the same syringe subassembly. In its preferred form, removable stop 102 comprises first and second semi-cylindrical collar portions 104 and 106 positioned around plunger stem 32 (FIG. 8).

In operation, apparatus 100 is loaded with a syringe subassembly and dislodged or fired substantially as described above. In this embodiment, however, stop 102 halts movement of plunger 30 prior to full discharge of the medication from ampule 22. More particularly, shoulder 34 of plunger 30 is depressed until it engages collar portions 104 and 106. This partial travel of plunger 30 is suitable to inject a first dose of the medication. If the user wishes to administer a second injection with the remaining medication, the user simply removes cap 14, withdraws the syringe subassembly from the barrel. This allows removal of the split collar which is easily removed due to the split design. The injector is then recocked by depressing the driver 40. The partially discharged syringe subassembly is reloaded into the barrel and the end cap 14 reinstalled. With stop 102 removed, apparatus 100 is now essentially identical to apparatus 10 and is ready for its second firing. When driver 50 is actuated, the plunger is forced further into ampule 22 to displace the remaining fluid medication out through needle 26.

Due to the construction of reloadable injector apparatus 100, the user can alternatively administer the second dose manually and without recocking and reloading the apparatus. The user can simply remove the syringe subassembly from the apparatus, take off the stop collars, and manually inject the medication using only the syringe subassembly. This is very useful in dire emergency situations where time is critical and cannot be wasted recocking and reloading the apparatus. In a similar fashion either embodiment 10 or 100 can be opened and the syringe subassembly removed to allow manual injection. This may be needed due to mechanical difficulties or for other reasons.

It should also be appreciated that the novel apparatus according to this invention can be employed to reduce or eliminate the loss of valuable medicines. Such medicines have previously been lost when used in emergency injectors. This occurs because of time deterioration and the fact that the medicine is sealed within the injector. The current invention can be employed in either of two ways to prevent such waste. Firstly, medicines can be installed only when needed and can be taken from regular inventories of the cartridges. Secondly, medicines used in the novel injectors can be installed and then removed in adequate time to allow the hospital or other medical service to use them in the normal course of providing services, thus preventing waste of the cartridge due to time deterioration. The injector is not lost merely because of medicine aging and can continue to serve standby or be reloaded.

FIG. 9 shows a preferred carrying case 110 which can be used in injector systems according to this invention. Case 110 is sized to house apparatuses 10 or 100. Case 110 has first and second halves 112 and 114 that frictionally mate to form a hollow, tubular enclosure. First half 112 has a foam pad 116 positioned at an end thereof to provide a buffering cushion to help prevent the apparatus from rattling or shifting within the case. A clip 118 that is mounted to the exterior of case 110. Clip 118 is similar to ball point pen clips and likewise, is suited for attaching case 110 to a shirt pocket or the like. Case 110 also includes a pocket area 120 for storing tablets 122, such as oral antihistamines.

FIG. 10 shows a reloadable injection apparatus 150 according to yet another preferred embodiment of this invention. Apparatus 150 is very similar to apparatus 10 of FIGS. 2–5, and only the different features will be described in detail.

Injection apparatus 150 has a modified distal, muzzle end cap 152 which is threadably coupled to muzzle end 72 of barrel 12. Modified end cap 152 is constructed with needle passageway 74 formed therein through which the needle can extend during injection. Apparatus 150 has a protective sheath 154 provided on needle 2(5. Sheath 154 protects and maintains the sterility of needle 26 and is preferably formed of plastic or rubber. Sheath 154 is sized to fit through needle passageway 74 of end cap 152.

Injector 150 also includes a sheath remover 15(5 for engaging and removing protective sheath 154 from needle 26. Sheath remover 156 is detachably connected to muzzle end 72 of barrel 12. Preferably, sheath remover 156 comprises a tubular section 158 which is opened at one end and an end wall 160. The tubular section 158 has a diameter at its inner surface that is approximately equal to the diameter of the outer surface of end cap 152 so that sheath remover 156 is frictionally mounted by sliding it onto end cap 1:52 at muzzle end 72. Other coupling arrangements, such as threaded couplings, are also possible. The sheath remover is preferably formed of a hard, durable material, such as plastic or metal.

Sheath remover 156 has a clenching aperture 162 formed in end wall 160. Aperture 162 is sized to receive and frictionally grip protective sheath 154. As sheath remover 156 is withdrawn from injection apparatus 150, the clenching aperture 162 grasps sheath 154 to simultaneously remove the sheath to expose needle 26 for injection. Alternatively, the sheath remover can be fitted with barbs (see FIG. 12) along aperture 162 to engage the sheath. This alternative construction is preferred when a rubber sheath is used.

FIG. 11 shows injection apparatus 150 stored in a protective carrying case 170 constructed according to a further aspect of this invention. Carrying case 170 is a hollow, substantially tubular assembly sized to hold apparatus 150. Case 170 is made of a front or lower part 172 and a rear or upper part 174. Parts 172 and 174 are manually detachable to allow removal of the injector apparatus 150. The lower part will normally hold the injector after the upper part 174 is removed. The front and rear casing pans have a frictional slide-fit coupling 176 for holding the two parts together in a manually detachable assembly.

Casing 170 also includes a Sheath remover holder 178. Sheath remover holder 178 frictionally engages sheath remover 156, such as by closely sizing the complementary surfaces, or providing a slight interference fit therebetween. Sheath remover holder 178 engages and holds the sheath remover 156 so that the protective sheath 154 is automatically removed from the needle when the injector is withdrawn from the lower part 172 of the case. In this manner, the injector is immediately ready for withdrawal of the safety and firing, thereby eliminating the additional step of removing the sheath. Alternatively, the case can be constructed without a sheath remover holder, and the sheath remover 156 and engaged sheath 154 can be manually removed after the injector has been removed from the case.

FIG. 12 is an enlarged view of the muzzle end of the encased injection apparatus and shows an alternative clasp-type sheath remover in more detail. The sheath remover includes a barbed clasp 180 which operably grasps sheath 154. Clasp 180 allows sheath 154 to be easily inserted therein, but resists removal of the sheath therefrom. In this manner, clasp 180 readily slides onto sheath 154 when the sheath remover 156 is installed over barrel 12 of injector 150. During unloading of injector 150 from casing 170, however, the clasp grips the sheath to thereby simultaneously remove the sheath as casing part 172 is taken from the muzzle end of barrel 12.

In the preferred construction, clasp 180 is a unidirectional clasp which permits easy insertion of the sheath in a first direction as casing part 172 is slid onto the injector, but resists withdrawal of the sheath in a second opposite direction when the casing part is slid off of the injector. Clasp 180 comprises multiple deflectable prongs 182 (e.g., four prongs) having barbed catches 184 at their inner tips. The barbed catches have sloped surfaces 186 which facilitate insertion of the sheath, and sharp inwardly directed points that grip the sheath once it is inserted into the clasp. Alternatively, the prongs can be converted to an annular ring or apron (not shown) but which would appear the same or similar in sectional view as the barbed prongs of FIG. 12.

FIG. 13 shows a reloadable injection apparatus 200 according to yet another preferred embodiment of this invention. Apparatus 200 is similar to apparatus 10 of FIGS. 2–5 and apparatus 150 of FIG. 10. Unlike these earlier versions, however, injector 200 has a trigger handle 202 connected to driver release 50. Trigger handle 202 is preferably in the form of a sleeve which forms the outer shell of the injector. The trigger handle sleeve is advantageously constructed as a cylindrical sleeve slightly larger in diametrical size than the barrel 12 and is slidable thereon.

The upper end of the trigger handle is preferably provided with an end wall 203. End wall 203 has an aperture 205 through which extends the safety pin 57 of safety 56. Aperture 205 also serves as a trigger release feature in the form of contracting surfaces 71 which bear upon and contract the tips 62 of the pronged driver catch. After removing safety 56, the trigger handle is slidable from rest to fire positions by moving trigger handle 202 left in FIG. 13 relative to barrel 12. The driver release 50 thus fires driver 40 as the trigger handle is moved to a fire position.

Trigger handle 202 includes a hand-fitting sleeve member 204 which fits over and slides upon barrel 12. Sleeve member 204 moves relative to barrel 12 from its rest or untriggered position to a fire or triggered position. Preferably, sleeve member 204 extends substantially along barrel 12 from its proximal end 13 toward its distal, muzzle end 72. Sleeve member 204 preferably extends at least 75% of the barrel length to a location adjacent to end cap 152. More preferably, sleeve member extends a sufficient length so as to abut the inward face edge of the sheath remover 156 when in the loaded but unfired condition. This abutting relationship serves as a safety feature in restricting longitudinal motion of the trigger sleeve in the armed condition, until the sheath remover and sheath have been removed from the muzzle end of the injector. Thus, even though the safety has been removed, the injector can in most situations only be fired after removing the sheath and sheath remover. The sheath remover thereby functions as a second safety in the construction shown.

FIG. 13 further shows that barrel 12 and trigger handle 202 can be constructed so as to retain the trigger handle on the barrel and provide mechanical interengagement therebetween. These functions are advantageously addressed in combination by a retainer in the form of one or more barrel retainers which engage with the trigger handle. As shown the barrel is provided with two complementary retaining dogs 242 which are received in receiving slots 241. The retaining dogs 242 are preferably provided with a lower face which is transverse in relationship to the longitudinal axis of the injector. The upper face is preferably angled to suggest a portion of a conical surface. These angled upper faces served to facilitate assembly of the trigger handle upon the barrel by inserting the barrel into the muzzle end of the trigger handle and distorting the respective parts a sufficient amount to bring the dogs into registration with receiving slots 241.

Slots 241 are formed into or through the wall of the trigger handle. The lower faces of the dogs bear upon the lower ends of slots 241 when the injector is in the loaded and unfired position. After the safety 56 has been removed then the trigger handle 204 can be depressed to slide the trigger relative to the barrel.

The dogs 242 and slots 241 also provide mechanical interengagement between the trigger handle and barrel. More specifically, the engagement prevents excessive longitudinal motion. It further prevents relative rotational motion between the barrel and trigger handle. This antirotation capability allows the end cap 152 to be twisted relative to the barrel while holding the trigger handle. This relative twisting is needed to remove and install the end cap relative to the barrel, such as during emergency manual use, or to load and unload the injector. This construction further allows the trigger handle to function more effectively in the capacities of being the manually grasped pan through which force is transferred to both insert and withdraw the needle into a person being injected.

The barrel and trigger handle are most preferably constructed of transparent material, such as transparent plastic. This construction allows the user to view into the injector to determine whether there is a cartridge in the injector. It also allows the user to determine whether the medicine in the ampule has become unsuitable, such as might be indicated by discoloration or cloudiness.

To fire injector 200, the user first detaches sheath remover 156, thereby simultaneously removing sheath 154. The user then removes safety 56 to place the injector in a ready state. The user grasps trigger handle 202 in the hand and administers the medication through a swift arm stroke which drives muzzle end 72 against the user's body at the desired point of injection. The barrel will stop upon contact with the user; but, the trigger sleeve will continue to travel, releasing driver 40. Under the force of primary spring 44, driver 40 injects needle 24 of syringe subassembly 20 into the user's tissue and dispenses a proper dosage of medication 24.

The trigger handle facilitates administration of the medication through an easy grasp-and-swing action. This is particularly useful for users who are in a weakened condition and less able to fire the more exacting "thumb" trigger described above.

It should be noted that the embodiments illustrated in FIGS. 10 and 13 are most preferably equipped with a stop system which controls and limits displacement of the syringe plunger. FIG. 10 illustrates that the preferred stop system utilizes a first stop 188 and a second stop 189. First stop 188 is a removable stop, preferably formed by complementary collar halves which extend around the plunger shaft. The upper end of the first stop is engaged by the plunger head 34. This controls the amount of medicine dispensed in a first dose. The split collar 188 is removed by removing the muzzle cap 152 and sliding the syringe subassembly from barrel 12. After the split collars have been removed, the second stop 189 serves to stop the plunger during administration of a second dose. The plunger head 34 bears upon second stop 189. The second stop is advantageously in the form of a non-removable annular piece held on the plunger shaft. Second stop 189 allows good control of the second dose volume which is dispensed.

FIG. 14 shows that the invention also contemplates a further injector system having a case 270 similar to case 170. Case 270 has an upper or first part 274 which is sized to frictionally engage with a lower or second pan 272. Case 270 is shown enclosing injector 200 as shown in FIG. 13. The bottom or lower end is advantageously provided with a tip receptacle 298 which receives the tip of the sheath without appreciable force being exerted upon the sheath. Case 270 is further provided with a tip cushion 299 adjacent to the tip receptacle 298. A case pocket clip 291 is provided to aid in supporting the case in a user's pocket. Case 270 can further include, as desired, additional medicaments, such as tablets 292.

FIG. 15 shows an alternative cartridge or syringe subassembly which can advantageously be used in injectors made in accordance with this invention. The cartridge of FIG. 15 has an adjustable plunger shaft 330. Adjustable plunger shaft 330 is advantageously constructed using a first plunger shaft piece 331. First plunger shaft piece 331 has a first or stopper connection feature which is advantageously in the form of a threaded receptacle 332 which receives a threaded connection stud 29 mounted to the syringe stopper. The first plunger shaft piece 331 also has a second or adjustment head connection feature advantageously in the form of a threaded shaft head receptacle 336. The plunger shaft head connection receptacle 336 receives a second plunger shaft piece 335, preferably in axially adjustable relationship. The axial adjustability is most preferably accomplished using a threaded connection which allows the head 335 to be screwed into and out of the receptacle to adjust the position of the contact head 334. This construction can be used to adjust for and accommodate for variations in the length of the syringe and the position of the stopper within the ampule. Head 334 is preferably adjusted by using a gauge (not shown) which indicates the desired position of the head and then by screwing the second plunger shaft piece 335 to achieve the desired head position. Stop 188 is advantageously chosen have a length equal to approximately half the distance between stop 189 and the contacting face of the plunger head 334 where the contents of the ampule are to be dispensed in two approximately equal doses.

The reloadable injection apparatus of this invention is advantageous because it affords maximum flexibility in that manual or automatic injection of a single or multiple dose of medication can be easily and conveniently administered. The invention also improves reliability because, in the event of mechanical failure with the injector, the user can easily access the syringe subassembly and manually inject the medication. These and other advantages and benefits of the invention are described or apparent from the description given herein.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A fluid medication injection apparatus comprising:
   a barrel having a cavity therein;
   a syringe subassembly within the barrel and sized to slide within the cavity, the syringe subassembly having an ampule for housing fluid medication, a needle, and a plunger having a plunger shaft, the plunger being operable to force the fluid medication from the ampule through the needle;
   a protective sheath provided on the needle;
   a driver having a driver shaft operable to detachably engage the plunger shaft for forcing the syringe subassembly to inject the needle and displace fluid medication through the needle, the driver being movable between a cocked position and extended positions;
   a driver release for controllably releasing the driver from the cocked position into an extended position; and
   a sheath remover for engaging and removing the protective sheath from the needle.

2. A fluid medication injection apparatus according to claim 1 wherein:
   the barrel has a muzzle end through which the needle passes during injection; and
   the sheath remover is detachably connected to the muzzle end.

3. A dual use fluid medication injection apparatus capable of both mechanically powered administration and manual administration of a fluid medication, comprising:
   a barrel having a cavity therein;
   a manually usable syringe subassembly positioned within the barrel and sized to slide within the cavity, the syringe subassembly having:
      an ampule for housing fluid medication;
      a needle in fluid communication with said ampule;
      a plunger for forcing the fluid medication from the ampule through the needle; said plunger including a plunger shaft and a plunger portion which extends from the ampule to allow manual depression of the plunger to dispense fluid from the ampule;
   said barrel including at least a first part and a second part which are manually detachable to allow removal and installation of the syringe subassembly;
   a driver having a driver shaft which is operable to detachably engage the plunger shaft, for forcing the syringe subassembly to inject the needle and displace fluid medication through the needle, the driver being movable between a cocked position and extended positions;
   said plunger being unattached to said driver to allow removal of said syringe subassembly from the barrel while in cocked or extended positions;
   a driver release for controllably releasing the driver from the cocked position into an extended position;
   a sheath remover for engaging and removing the protective sheath from the needle.

4. In an injection apparatus having a syringe subassembly and a driver having a driver shaft operable to displace medication therefrom, the syringe subassembly, comprising:
   an ampule for housing fluid medication;
   a needle capable of fluid communication with said ampule;
   a plunger for forcing the fluid medication from the ampule through the needle; said plunger having a plunger shaft adjustable in length to adjust a desired dose amount which will be dispensed, the plunger shaft being engaged by the driver shaft of the driver when the fluid medication is forced from the ampule;
   wherein said plunger shaft includes a first plunger shaft part and a second plunger shaft part which is axially adjusted relative to said first plunger shaft part.

* * * * *

UNITED STATES PATENT AND TRADEMARK OFFICE
CERTIFICATE OF CORRECTION

PATENT NO. : 5,665,071
DATED : September 9, 1997
INVENTOR(S) : Ronald E. Wyrick

It is certified that error appears in the above-identified patent and that said Letters Patent is hereby corrected as shown below:

At column 2, line 30, change "latter" to --later--.

At column 8, line 62, change "2(5" to --26--.

At column 8, line 66, change "15(5" to --156--.

At column 9, line 7, change "1:52" to --152--.

At column 9, line 30, change "pans" to --parts--.

At column 11, line 12, change "pan" to --part--.

At column 11, line 58, change "pan" to --part--.

Signed and Sealed this

Twenty-seventh Day of January, 1998

Attest:

BRUCE LEHMAN

Attesting Officer

Commissioner of Patents and Trademarks